(12) United States Patent
Naimark et al.

(10) Patent No.: US 7,611,482 B2
(45) Date of Patent: Nov. 3, 2009

(54) MINIMALLY-INVASIVE SMART DEVICES

(75) Inventors: Wendy Naimark, Cambridge, MA (US); Henry Tung, Hopkinton, MA (US); Maria Palasis, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 533 days.

(21) Appl. No.: 10/300,881

(22) Filed: Nov. 21, 2002

(65) Prior Publication Data

US 2004/0102733 A1 May 27, 2004

(51) Int. Cl.
*A61M 31/00* (2006.01)
(52) U.S. Cl. .................. 604/65; 604/99.01; 606/194
(58) Field of Classification Search ............. 604/65–67, 604/100.01, 103.06–103.08, 103.01–103.02, 604/96.01, 97, 97.01, 890.1, 891.1, 93.01, 604/99.01–99.04; 600/488, 466; 606/14, 606/41, 52, 76, 205, 7, 13, 27–29, 32, 191–192, 606/194
See application file for complete search history.

(56) References Cited

U.S. PATENT DOCUMENTS

| | | | | |
|---|---|---|---|---|
| 4,403,984 A | * | 9/1983 | Ash et al. | 604/503 |
| 5,046,497 A | * | 9/1991 | Millar | 600/309 |
| 5,291,607 A | * | 3/1994 | Ristic et al. | 713/300 |
| 5,431,628 A | * | 7/1995 | Millar | 604/100.01 |
| 5,893,881 A | * | 4/1999 | Elsberry et al. | 607/5 |
| 6,245,026 B1 | * | 6/2001 | Campbell et al. | 600/549 |
| 6,256,533 B1 | * | 7/2001 | Yuzhakov et al. | 604/21 |
| 6,309,370 B1 | * | 10/2001 | Haim et al. | 604/66 |
| 6,592,519 B1 | * | 7/2003 | Martinez | 600/309 |
| 6,626,899 B2 | * | 9/2003 | Houser et al. | 606/14 |
| 6,692,494 B1 | * | 2/2004 | Cooper et al. | 606/46 |
| 6,733,459 B1 | * | 5/2004 | Atsumi | 600/488 |
| 6,860,867 B2 | * | 3/2005 | Seward et al. | 604/22 |
| 2002/0026138 A1 | | 2/2002 | Cowan, Jr. et al. | |

FOREIGN PATENT DOCUMENTS

| | | |
|---|---|---|
| DE | 101 20 280 | 12/2001 |
| EP | 0 251 512 B1 | 8/1994 |
| EP | 1 078 644 | 2/2001 |
| JP | 04041420 A * | 2/1992 |
| WO | WO 89/01794 | 3/1989 |
| WO | WO 02/068036 A1 | 9/2002 |

OTHER PUBLICATIONS

Wilson, Charles, Sensors in Medicine, Nov. 13, 1999.*

(Continued)

*Primary Examiner*—Nicholas D Lucchesi
*Assistant Examiner*—Theodore J Stigell
(74) *Attorney, Agent, or Firm*—Kenyon & Kenyon LLP

(57) ABSTRACT

There is provided a minimally-invasive smart device which can detect environmental conditions in the vicinity of a target site within a patient's body and autonomously determine whether the medical device on the distal end of the instrument should be activated to perform, or inhibited from performing, a desired minimally-invasive medical procedure. The smart device includes a medical device affixed to the distal end of a lumen, at least one environmental condition sensor adapted to detect an environmental condition adjacent to the medical device, and at least one medical device actuator which responds to signals from an environmental condition sensor to either cause the medical device to perform the desired medical procedure or to inhibit operation of the medical device actuator.

23 Claims, 3 Drawing Sheets

OTHER PUBLICATIONS

Mayo Clinic Staff, "Pacemakers: Generating regular heatbeats" [online],Oct. 13, 2006 [retrieved Dec., 11 2006]. Retrieved from the Internet:<URL: www.mayoclinic.com/health/pacemakers/HO01165>.

"Implantable Cardioverter Defibrillator" [online], [retrieved Dec. 11, 2006]. Retrieved from the Internet <URL: http://www.216,185,112.5/presenter.jhtml?identifier=11227>.

Gasparini el al.. "Endocardial Implantation of a Cardioverter-Defibrillator in a 13-Month-Old Child Affected by Long-QT Syndrome and Syndactyly." *Circulation*, 2004, 110:e525-e527 [online]. American Heart Association, Inc. [Retrieved Dec. 4, 2006]. Retrieved from the Internet <URL: http://www.circ.ahajournals.org/cgi/content/full/110/23/e525>.

European Office Action dated Nov. 6, 2006.

* cited by examiner

MINIMALLY-INVASIVE SMART DEVICES

TECHNICAL FIELD

The present invention regards environmental sensing and control of the activation of minimally-invasive devices within a patient's body. More specifically, the present invention regards a device and method for intelligent sensing of localized conditions in the vicinity of a minimally-invasive instrument within a patient's body and control of the actuation of devices such as valves or needles affixed to the minimally-invasive instrument to permit high precision deployment of substances such as therapeutic agents or activation of apparatus such as balloon catheters or biopsy forceps during minimally-invasive procedures.

BACKGROUND

The deployment in the body of medications and other substances, such as materials useful in tracking biological processes through non-invasive imaging techniques, is an often repeated and advantageous procedure performed during the practice of modem medicine. Such substances may be deployed in either case through non-invasive procedures such as endoscopy and vascular catheterization, as well as through more invasive procedures that require larger incisions into the body of a patient. The non-invasive and less-invasive procedures are generally used when the target area is accessible through a lumen of the body, while the more invasive procedures may be employed when the target area is located deep within the body or otherwise not readily accessible through a lumen of the body.

Previously, during performance of procedures such as endocardial injection or infusion, angioplasty, or biopsy of tissue or fluids, minimally-invasive medical instruments have primarily been steered by physicians to the location within the patient's body at which the procedure was to be performed, using, for example, images from optical devices located at the end of the instruments' lumens or from non-invasive imaging techniques (e.g., x-ray imaging). Once placed at the desired site, the device at the distal end of the instrument would be actuated by the physician to perform the procedure (e.g., injection or infusion, balloon inflation, sample collection). Ideally, the medical device would be actuated precisely at the desired target site, such as in FIG. 1, which illustrates the ideal situation in which a prior art infusion device 1 affixed to lumen 2 is ideally positioned within a blood vessel 3 such that a therapeutic substance 4 is infused directly to the target cells.

In practical applications, however, placement of the distal end of the medical instrument at the desired location within the patient's body requires careful, time-consuming monitoring of the placement of the instrument tip within the body. Even with such care, however, limitations on the quality of the available images and obstruction of views by surrounding tissues or fluids can degrade the accuracy of placement of the instrument. Such difficulties can result in less than optimal injection, infusion, inflation or sample collection.

Moreover, even if positioned properly, the instrument might be aligned with areas in which performance of the medical procedure would not be desired, such as where an asymmetric plaque deposit inside a blood vessel would render infusion delivery or angioplasty ineffective or potentially dangerous. An example of such a situation is illustrated in FIG. 2. FIG. 2 is a side view of an angioplasty balloon 5 of a type well known in the art affixed to lumen 6, positioned within a blood vessel 7 in a location where the medical device has encountered non-uniform conditions. On one side 8 of the blood vessel, the target of the therapeutic substance to be delivered by balloon 5, the endothelial cells line the vessel wall, are in contact with balloon 5 and the desired infusion of the therapeutic substances may proceed. Attached to the other side 9 of blood vessel 7, however, is a common eccentric lesion 10, here shown attached to the vessel and in contact with balloon 5. Due to the presence of lesion 10, the therapeutic substance is blocked from reaching the wall of blood vessel 7, rendering this minimally-invasive surgical procedure ineffective in the region of the lesion.

In view of the problems of the prior art with manual placement and actuation of medical devices during minimally-invasive surgical procedures, there exists a need for an apparatus and method for achieving intelligent, highly precise actuation of minimally-invasive medical devices at target locations within a patient's body.

SUMMARY OF THE INVENTION

The present invention is directed to address the foregoing concerns with previous minimally-invasive catheter and endoscopy systems. In one embodiment of the present invention, there is provided a so-called "smart" minimally-invasive device which can detect environmental conditions in the vicinity of a target site within a patient's body and autonomously determine whether the medical device on the distal end of the instrument should be activated to perform, or inhibited from performing, a desired medical procedure. The smart device includes a medical device adapted to be affixed to the distal end of a lumen, at least one environmental condition sensor adapted to detect an environmental condition adjacent to the medical device, and at least one medical device actuator which responds to signals from an environmental condition sensor to either cause the medical device to perform the desired medical procedure or to inhibit operation of the medical device actuator. The apparatus may be equipped to inhibit sensing and/or actuation of the medical device actuators until the device has been maneuvered to the vicinity of the target site, for example by use of retractable device covers or inhibition of electrical signals to the medical device actuators.

The embodiments of the medical device and the medical device actuator in the present invention include a variety of apparatus for performing minimally invasive medical procedures, such as: a device and actuator that dispenses therapeutic agents or other substances from the device housing by opening a port or a valve or by extending a needle into a target area and infusing or injecting a substance into the target area; a device and actuator for balloon inflation as during an angioplasty or stent deployment procedure; or a device and actuator for taking a biopsy tissue or fluid sample. These devices and actuators would be equally suitable for use with a variety of minimally-invasive lumens, including catheters and endoscopes.

The sensors used in the embodiments of the present invention may include a variety of technologies as suited to the nature of the minimally-invasive medical procedure to be performed, including mechanical, biological, electrical, piezoelectric, magnetic and thermal sensors, as well as combinations thereof. The sensors and the mechanical device actuators further may utilize micro-electromechanical systems technology to facilitate their incorporation into a lumen-mounted medical device with sufficient precision and sensitivity to the target environment.

The present invention further includes a method for utilizing the foregoing apparatus to ensure a minimally-invasive medical procedure is performed at a desired location. The method includes inserting the foregoing apparatus comprising a minimally-invasive medical device affixed to the distal end of a lumen, maneuvering the medical device to the target area using techniques well known to practitioners in the minimally-invasive surgical procedures art, and moving the medical device about the target area to permit the sensors on the medical device to precisely identify an appropriate location for activation of the actuators on the medical device which cause the desired minimally-invasive procedure to be performed.

The present invention provides highly localized and controllable delivery of therapeutic agents or high precision activation of medical apparatus, such as balloon catheters and biopsy forceps, at a target site within a patient. This invention further provides the advantages of enabling highly concentrated delivery of therapeutic agents into target tissues or organs, and does so in a manner that results in minimal perturbation of fragile surrounding tissues.

DETAILED DESCRIPTION

Figure 3:
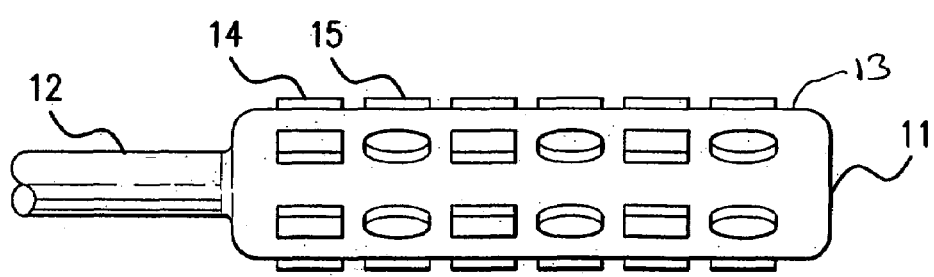
FIG. 3 is a side view of a medical device of a first embodiment of the present invention, schematically showing a plurality of sensors and a plurality of medical device actuators on an outer peripheral surface of the device.
Figure 4:
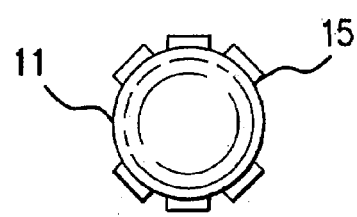
FIG. 4 is a schematic end view of a medical device shown in FIG. 3.

The present invention is adaptable to a broad variety of minimally-invasive medical apparatus and procedures. A first embodiment of the present invention is shown in FIG. 3. FIG. 3 illustrates an infusion catheter 11 affixed to lumen 12, where infusion catheter 11 is equipped on an outer peripheral surface 13 with a plurality of sensors 14 and a plurality of medical device actuators 15. An end view showing the distribution of actuators 15 around outer peripheral surface 13 is shown in FIG. 4. The location of the sensors and the actuators shown in FIG. 3 and FIG. 4 are only intended to be schematic illustrations of the distribution of these components about the outer surface 13, as both the sensors and the actuators may be distributed about the surface as needed for efficient performance of the minimally-invasive medical procedure. Further, the sensor and actuator components may be co-located or combined into a single sensor-actuator unit, as described in the second embodiment, below. For perspective, the sensors and actuators of this embodiment are micromechanical devices, with scales on the order of micrometers to nanometers.

The medical device of this embodiment is inserted into a patient's body and maneuvered to a target area using techniques well known in the minimally-invasive surgical arts. During the insertion and maneuvering process, the sensors 14 on the device may be active, or, if desired to preclude premature actuation of the medical device, may be inhibited from operating until the medical device reaches the target infusion area. Examples of approaches to inhibiting actuation during transit include maintaining the medical device in a protective sleeve during maneuvering and then deploying the device from the sleeve upon reaching the target area, or by blocking transmission of signals (such as electrical impulses) from the sensors that would trigger actuator activation and then enabling signal transmission on reaching the target area.

The sensors 14 are adapted to detect a predetermined environmental condition in the vicinity of the medical device. In the present embodiment, an application where a therapeutic substance is to be delivered to a blood vessel, the sensors are micro-mechanical devices that respond to inverse pressure differentials. These sensors signal the opening of the medical device actuators 15 (infusion ports or valves) to release the therapeutic substance when the sensors 14 detect a predetermined low pressure outside the medical device. Conversely, when sensors 14 detect high pressure outside the medical device, the infusion ports or valves remain closed to preclude infusion into undesired areas.

The sensors 14 and actuators 15 of the first embodiment are not limited to a specific form of linkage to their respective actuators. In the present embodiment, physical movements of the sensors serve to cause the actuators 15 to open or close, however, different sensors with a variety of outputs may serve as activation or inhibition signals, such as electrical signals transmitted to the actuators. Sensor signals also may be transmitted to a controller (not shown) located either within the medical device or a remote location outside the patient's body, and processed for transmission to the appropriate actuators on the medical device. Thus, while the sensors may contain mechanical elements whose movements directly impinge on or are otherwise mechanically linked to the medical device actuator (or multiple actuators), the sensors also may generate electrical impulses that either directly energize the actuators or send signals to intermediate control electronics, either on or remote from the medical device, which in turn send signals to the medical device actuators.

Figure 1:
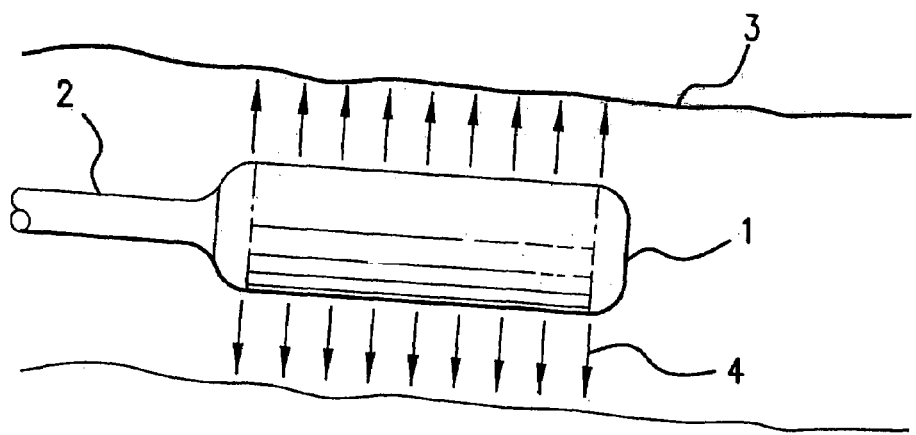
FIG. 1 is a side view of an infusion device showing its use within a blood vessel to perform a therapeutic substance infusion procedure.
Figure 2:
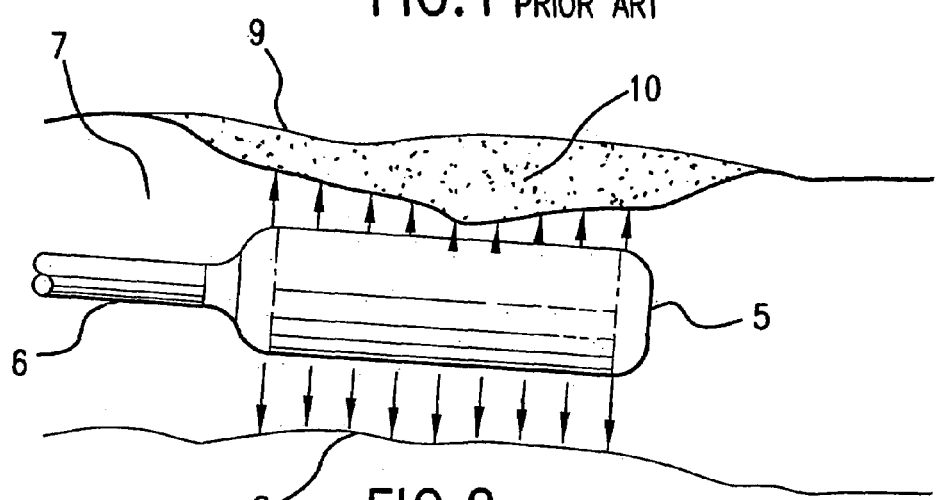
FIG. 2 is a side view of an angioplasty balloon of a type well known in the art within an arterial vessel showing areas of successful infusion and unsuccessful infusion during an angioplasty procedure in the presence of an arterial lesion.

Importantly, the plurality of sensors 14 and plurality of actuators 15 in the first embodiment are grouped such that the actuators on one portion of the infusion catheter respond to a subset of the sensors, while the actuators on the other portions of the catheter respond to other subsets of the sensors. In this way, the medical device of this embodiment has the capability to selectively sense a first environmental condition and actuate infusion of the therapeutic substance only in the specific regions about the medical device in which infusion is desired, while also being capable of sensing a second environmental condition corresponding to a region in which infusion is not desired, such as into an eccentric lesion like that depicted in FIG. 2, and inhibiting actuator operation accordingly. This selective activation and inhibition feature may also be provided though the use of two different types of sensors, such as pressure sensors to detect a first environmental condition (in this example, differential pressure) and biological sensors (discussed further, below) to detect a second environmental condition (for example, a lesion). The sensors 14 and actuators 15 also may be grouped into subsets that do not require a one-to-one correspondence between the number of sensors and actuators, as either a single sensor may control activation or inhibition of several actuators, or a single actuator may be activated by any of a plurality of sensors.

Figure 5:
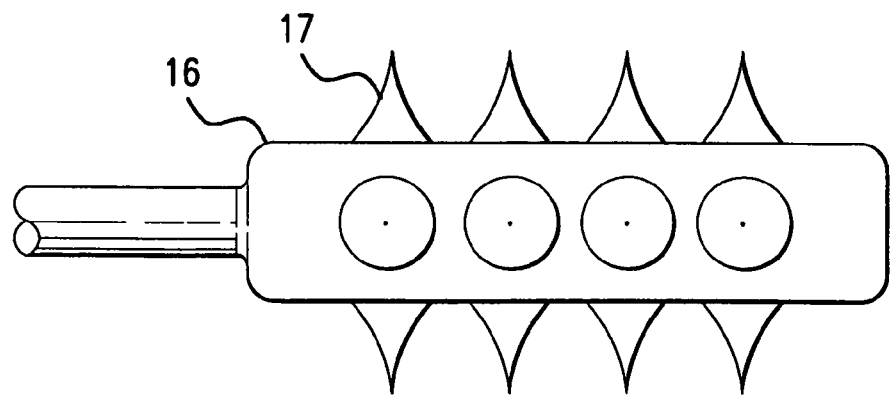
FIG. 5 is a side view of a medical device of the first embodiment of the present invention, showing a plurality of pressure-sensitive sensors and infusion ports affixed to the outer surface of the medical device.
Figure 6:
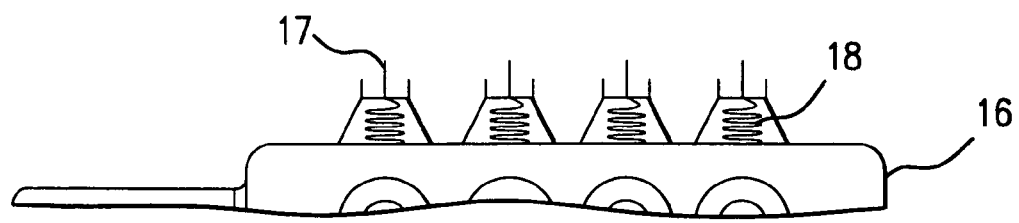
FIG. 6 is a cross-section view of an outer peripheral surface of a medical device of the first embodiment of the present invention, showing a plurality of combined sensor and actuator infusion needle devices affixed to the outer surface of the medical device.

The sensors used in the present invention are not restricted to the pressure sensors of the first embodiment. On the contrary, the choice of sensor is determined by the minimally-invasive medical procedure to be performed. For example, where the medical device is to be placed at a target site where differentiation between soft and firm tissues is required, a pressure-sensitive sensor may be employed, such as those shown in FIG. 5 and FIG. 6. FIG. 5 illustrates infusion nozzles 16 on the surface of medical device 11, equipped with contact-sensing probes which have been tuned to respond to predetermined levels of axial and/or transverse force. As shown in the cross-sectional view of the nozzles in FIG. 6, sensing probe 17 is biased in the nozzle-closed position by a spring 18, whose force can be varied to tune the response of probe 17 to the target environment. Other physical contact sensors include sensing probes affixed to piezoelectric crystals which generate an electric current upon displacement of the probe.

The sensors employed in the present invention can also include sensors for biological conditions. For example, sensors that detect nitric oxide could be used to detect the presence of an intact endothelium, whereupon, if the objective is to inject a therapeutic substance into endothelial cells, the sensors could signal for the actuators to cause the desired infusion or injection to occur precisely at the desired site.

Other sensors employing detection of biological conditions may also be employed. Sensors which detect pH could be used to detect a, macrophage-rich lesion or a smooth cell proliferative area while electrostatic sensors could be employed to identify regions where elements such as calcium is present. Similarly, sensors that detect hydrophobic interactions could precisely identify locations of lipid deposition for appropriate treatment. Biological sensors also can include the coating of sensors with receptor ligands for the detection of endothelial cell integrins, where cell binding recognition could signal activation of the medical device, or with monoclonal antibodies for targeting lipoproteins, for example, to detect lipid associated atheroma to prevent delivery of therapeutics in such an area. Other non-cardiac applications include use of oxygen detecting sensors in treatment of cancerous tumors to differentiate hypoxic tissue from normal tissue, temperature sensors for detection of elevated temperature cancerous tissues, and force transducer sensors, such as atomic force microscopy tips, to detect biomechanical differences between normal and necrotic tissues.

Figure 7:
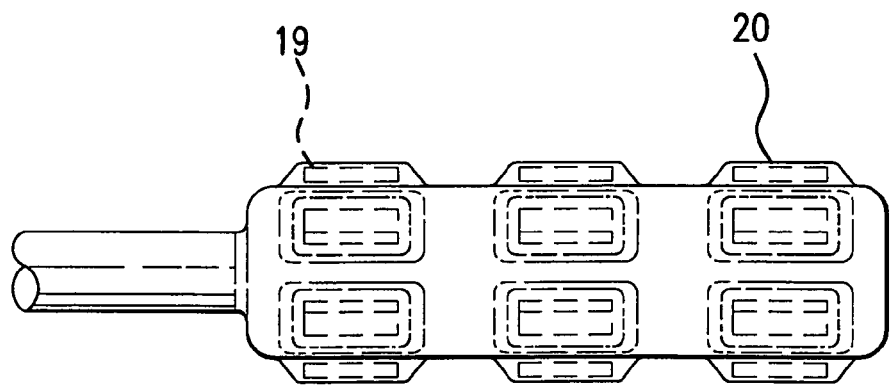
FIG. 7 is a side view of a medical device of the first embodiment of the present invention, schematically showing a plurality of sensors under a sheath over an outer peripheral surface of the medical device.

In addition to the foregoing sensor types, other sensor technologies may also be beneficially utilized with the present invention, including some which do not require direct immersion in the biological environment at the surface 13 around the medical device. Examples of this latter type of sensor are thermal sensors adapted to detect temperature differentials, such as in areas of abnormally low blood flow or high vascular infusion. These sensors do not require placement on the outer surface of the medical device; they may alternatively be placed under an outer sheath over the medical device as illustrated in FIG. 7 (sensors 19 shown indicated by broken lines under medical device sheath 20) or below the surface of the device itself. Similarly, magnets may be used to detect localized magnetic anomalies, as from injected or implanted magnetic substances, and may be mounted on or beneath the surface of the medical device and still provide for high precision actuation of the medical device.

Figure 8:
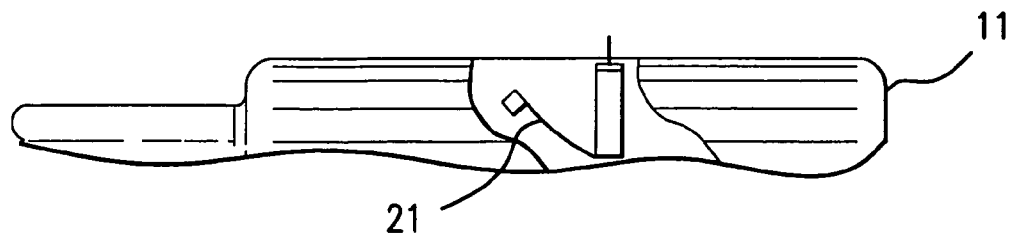
FIG. 8 is a cross-section view of a medical device of the first embodiment of the present invention, showing medical device actuators comprising a deployable injection needle beneath an outer peripheral surface of the medical device.
Figure 9:
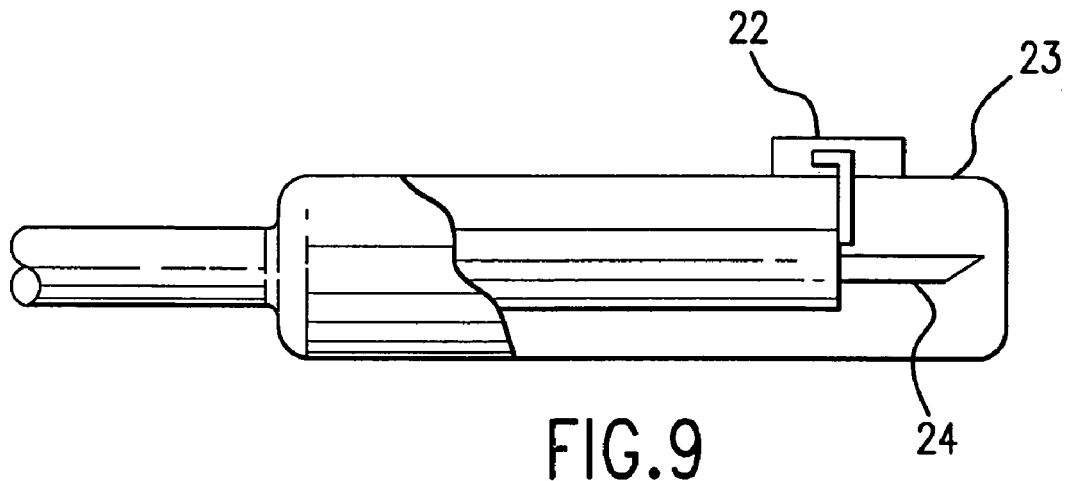
FIG. 9 is a cross-section view of a medical device of the present invention schematically showing a catheter with a deployable needle-tipped inner lumen, releaseably held by a needle release actuator.

As with the plurality of sensors 14 in the first embodiment, a variety of actuators may be employed in place of the medical device actuators 15 in the first embodiment, depending on the nature of the minimally-invasive medical procedure to be performed. As shown in FIG. 8, medical device 11 may be equipped with injection needle deployment actuators 21 which, on receipt of a signal from a sensor (or a controller responding to a signal from a sensor), causes a needle (or needles) to extend from medical device 11 into target tissue to permit therapeutic agent injection. Alternative actuators also include a biopsy needle release 22 as shown in FIG. 9 which permits a biopsy needle 24 to extend from medical device 23 into the biopsy target area for sample collection, and biopsy forceps for collection of biopsy tissue samples.

Figure 10:
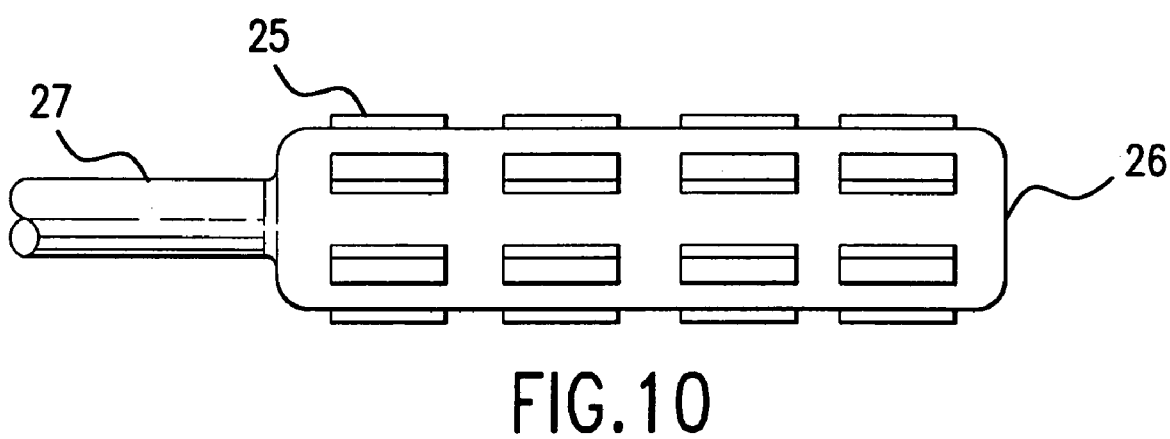
FIG. 10 is a side view of a second embodiment of the present invention, showing a medical device equipped with combined sensor and actuator units affixed to the outer surface of the medical device.

A second embodiment of the present invention is shown in FIG. 10, wherein the sensor and medical device actuator have been combined in order to minimize mounting space requirements and cost. In this embodiment, the combination sensor/actuator units 25 are mounted on a medical device 26, which in turn is affixed to lumen 27 in a manner similar to that of the first embodiment. The space savings realized by the use of combined sensor/actuator units provides the medical device designer a number of options for optimizing a medical device, depending upon the target application. The small combined sensor/actuator unit permits a higher density of sensors and actuators on the surface of the medical device, thus increasing the medical device's ability to accurately discriminate between desired and undesired infusion locations. In the event such a high level of discrimination is not required, the lower cost of the combined sensor/actuator units permits a suitable medical device to be constructed at a lower cost. Alternatively, the smaller combined sensor/actuator units would allow the medical device body may be made smaller, thereby improving its utility in a greater number of minimally-invasive medical procedures. The combined sensor/actuator units in the particular case of the second embodiment are contact sensors with a direct mechanical linkage between the sensor and the infusion port covers that block flow from an infusion ports. One of skill in the art should recognize that various types of combined sensors and actuators may be substituted for the present units, in response to the demands of a different environment about a medical device to be used in a different target area.

Figure 11:
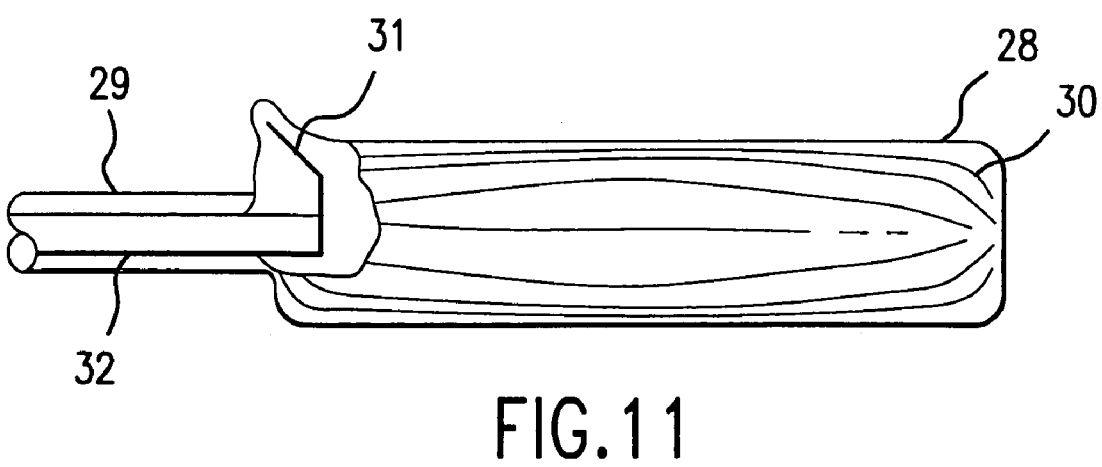
FIG. 11 is a side view of a third embodiment of the present invention, schematically showing a balloon catheter medical device with an inflatable balloon and a combined sensor and actuator controlling operation of an inflation port.

A third embodiment of the present invention is schematically illustrated in FIG. 11. In this embodiment, medical device 28 is an inflatable angioplasty balloon affixed to a lumen 29. Medical device 28 comprises an expandable membrane 30 of a type well known in the art, and a combination sensor/actuator unit 31 underneath the surface of the angioplasty balloon which controls the admission of an inflating fluid through inner lumen 32 within lumen 29. In this embodiment, when the probe of combined sensor/actuator 31 is depressed by contact with a target region, the port cover portion of combined sensor/actuator 31 uncovers the distal end of inner lumen 32, thereby permitting the introduction of an inflating gas or liquid into balloon 28. Upon completion of the balloon expansion procedure, the inflating fluid may be withdrawn through the uncovered end of inner lumen 30 until combined sensor/actuator 31 returns to the closed position, thus allowing the balloon to contract sufficiently to permit its withdrawal from the patient.

As with the forgoing embodiments, the specific sensors and/or actuators that may be employed in this third embodiment are not limited to the combination probe and port cover shown depicted in FIG. 11, but instead may include a number of alternatives, including biological sensors affixed to the outer surface of the balloon to detect a predetermined biological environment, separate sensors and actuators to permit individual inflation of segmented inflation chambers, and separate actuators that are only connected to a sensor via electrical connections or an intermediate controller (not shown). Further, the medical device 26 of this embodiment may also be equipped with a second sensor for responding to a second environmental condition which autonomously determines when inflation of the balloon should be terminated (for example, when a contact pressure between the balloon and the target site reaches a limit) and generates a signal to command an actuator to close off or otherwise halt the flow of the inflating fluid. Moreover, the inflatable balloon device of this embodiment may also be employed as a expansion balloon for an expandable stent (with or without a coating so long as the sensor's exposure to the environmental conditions in the vicinity of the medical device is not thwarted by the placement of the stent over the uninflated balloon. This latter concern can be addressed by placement of the sensors on the balloon in areas not underneath the unexpanded stent (for example, near the lumen end or the distal end of the balloon), or on the outside surface of the stent, either directly exposed to the target site or under a protective sheath over the unexpanded stent. In this latter case, the sensors would have to be equipped with elements which can release themselves from the balloon as the balloon is deflated.

The present invention also encompasses methods for using the foregoing apparatus in performing a minimally-invasive surgical procedure. As a first step in the method, a physician inserts into the patient a medical device affixed to a lumen and equipped with at least one sensor adapted to detect at least one predetermined environmental condition at the target location within the patient, and with at least one actuator adapted to initiate performance of the desired medical procedure upon detection of the predetermined environmental condition. The physician maneuvers the medical device and lumen using well known minimally-invasive surgical techniques to a desired location within the patient's body. Once in the vicinity of the target location, the physician moves the medical device until at least one sensor detects the predetermined environmental condition adjacent to the medical device. On detection of the predetermined environmental condition, the sensor generates a signal which is used to activate at least one medical device actuator and thereby initiate performance of the desired minimally-invasive medical procedure by the medical device. Following performance of the desired procedure, the lumen and medical device may be withdrawn from the patient.

During use of the foregoing method, at least one other sensor may also be adapted to detect a second predetermined environmental condition adjacent to the medical device, and if the second predetermined environmental condition is detected, the at least one other sensor may generate a signal inhibiting actuation of at least one medical device actuator to preclude performance of the desired minimally-invasive medical procedure at an undesired location.

Further, the medical device may be adapted to ensure the at least one sensor is inactive or otherwise inhibited, such as by encapsulation under a protective sheath, to ensure the medical device is not inadvertently activated before it reaches the target location within the patient's body. In the event the medical device is so adapted, the additional step of activating or freeing the at least one sensor must be performed once the medical device is at the target location within the patient.

The foregoing method may also be performed using a medical device of the present invention equipped with a plurality of sensors and a plurality of medical device actuators, and, if so adapted, the use of the method permits the desired minimally-invasive medical procedure to be performed in a highly precise and selective manner with subsets of the plurality of sensors either signaling for actuation or inhibition of subsets of the plurality of medical device actuators. Use of this method thus provides highly localized and controlled delivery of therapeutic agents or high precision activation of medical apparatus, such as balloon catheters and biopsy forceps, at a target location within a patient during minimally-invasive medical procedures, while minimizing perturbation of fragile surrounding tissues.

While the present invention has been described with reference to what are presently considered to be preferred embodiments thereof, it is to be understood that the present invention is not limited to the disclosed embodiments or constructions. On the contrary, the present invention is intended to cover various modifications and equivalent arrangements, including additional applications within the minimally-invasive surgical art in which autonomous actuation of medical devices may achieve improved. In addition, while the various elements of the disclosed invention are described and/or shown in various combinations and configurations, which are exemplary, other combinations and configurations, including more, less or only a single embodiment, are also within the spirit and scope of the present invention.

What is claimed is:

1. A medical device instrument comprising:
   an autonomous minimally invasive medical device on a distal portion of the medical device instrument, the medical device comprising:
   a first environmental condition sensor carried by the minimally invasive medical device adapted to detect a first environmental condition at a target site in the body of a patient adjacent to the medical device and adapted to transmit a first signal based on the first environmental condition; and
   a second environmental condition sensor carried by the minimally invasive medical device adapted to detect a second environmental condition at the target site in the body of the patient adjacent to the medical device and adapted to transmit a second signal based on the second environmental condition; and
   a plurality of actuators comprising:
   a first actuator carried by a first portion of the medical device adapted to receive the first signal and to actuate to deliver therapy to the patient at the target site if the first signal meets a first predetermined condition and to inhibit actuation if the first signal does not meet the first predetermined condition;

a second actuator carried by a second portion of the medical device adapted to receive the second signal and to actuate to deliver therapy to the patient at the target site if the second signal meets a second predetermined condition and to inhibit actuation if the second signal does not meet the second predetermined condition, wherein the plurality of environmental condition sensors and the plurality of actuators cooperate to autonomously determine whether to actuate the first actuator and the second actuator of the medical device, and wherein the first signal, the second signal, or both is a mechanical signal.

2. The medical device instrument of claim 1, wherein the medical device instrument is one of an infusion catheter and an injection catheter.

3. The medical device instrument of claim 1, wherein the first actuator, the second actuator, or both is one of a valve and a needle deploying device.

4. The medical device instrument of claim 1, wherein the medical device instrument is a balloon catheter.

5. The medical device instrument of claim 4, wherein the first actuator permits the balloon to be inflated.

6. The medical device instrument of claim 1, wherein the first environmental condition sensor, the second environmental condition sensor, or both is a mechanical sensor.

7. The medical device instrument of claim 6, wherein the mechanical sensor is a pressure sensor.

8. The medical device instrument of claim 6, wherein the mechanical sensor is a differential pressure sensor.

9. The medical device instrument of claim 6, wherein the at least one mechanical sensor is a pressure-sensitive sensor that has a contact-sensing probe tuned to respond to axial force, transverse force, or both.

10. The medical device instrument of claim 1, wherein the medical device is adapted to be affixed to a distal end of an endoscope during a minimally-invasive medical procedure.

11. The medical device instrument of claim 1, wherein the first and second sensors are different types of sensors.

12. A medical device instrument comprising:

an autonomous minimally invasive medical device on a distal portion of the medical device instrument, the medical device comprising:

at least one environmental condition sensor carried by the medical device adapted to detect an environmental condition adjacent to the medical device and adapted to transmit a signal based on the environmental condition; and at least one needle-deploying actuator carried by the medical device adapted to receive the signal transmitted from the sensor and deploy a needle from the medical device, wherein the at least one environmental condition sensor and the at least one needle-deploying actuator cooperate to autonomously determine whether to deploy a needle from the medical device, and wherein the signal is a mechanical signal.

13. The medical device instrument of claim 12, wherein the medical device instrument is one of an infusion catheter and an injection catheter.

14. The medical device instrument of claim 12, wherein the at least one environmental condition sensor is a mechanical sensor.

15. The medical device instrument of claim 14, wherein the mechanical sensor is a pressure sensor.

16. The medical device instrument of claim 14, wherein the mechanical sensor is a differential pressure sensor.

17. The medical device instrument of claim 14, wherein the at least one mechanical sensor is a pressure-sensitive sensor that has a contact-sensing probe tuned to respond to axial force, transverse force, or both.

18. An autonomous minimally invasive balloon catheter comprising:

at least one environmental condition sensor carried on a balloon of the balloon catheter adapted to detect an environmental condition adjacent to the balloon catheter and adapted to transmit a signal based on the environmental condition; and at least one actuator carried on a balloon of the balloon catheter adapted to receive the signal transmitted from the sensor to permit the inflation of the balloon, wherein the at least one environmental condition sensor and the at least one actuator cooperate to autonomously determine whether to permit inflation of the balloon, wherein the sensor and actuator are physically linked, and wherein the signal is a mechanical signal.

19. The balloon catheter of claim 18, wherein the at least one environmental condition sensor is a mechanical sensor.

20. The balloon catheter of claim 19, wherein the mechanical sensor is a pressure sensor.

21. The balloon catheter of claim 19, wherein the mechanical sensor is a differential pressure sensor.

22. The balloon catheter of claim 19, wherein the at least one mechanical sensor is a pressure-sensitive sensor that has a contact-sensing probe tuned to respond to axial force, transverse force, or both.

23. The balloon catheter of claim 18, further comprising means for inhibiting activation during transit.

* * * * *

UNITED STATES PATENT AND TRADEMARK OFFICE
CERTIFICATE OF CORRECTION

PATENT NO. : 7,611,482 B2  Page 1 of 1
APPLICATION NO. : 10/300881
DATED : November 3, 2009
INVENTOR(S) : Naimark et al.

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 671 days.
Column 1, line 23, "modem medicine" should be changed to --modern medicine--;
Column 5, line 17, "though" should be changed to --through--;
Column 5, line 54, "a, macrophage-rich" should be changed to --a macrophage-rich--;
Column 6, line 54, "may be" should be changed to --to be--;
Column 6, line 60, "ports" should be changed to --port--
Column 7, line 10, "balloon 28" should be changed to --expandable membrane 30--;
Column 7, line 12, "inner lumen 30" should be changed to --inner lumen 32--;
Column 7, line 27, "medical device 26" should be changed to --medical device 28--; and
Column 8, line 42, "improved" should be changed to --improvement--.

Signed and Sealed this

Tenth Day of August, 2010

David J. Kappos
*Director of the United States Patent and Trademark Office*